US012276628B2

(12) United States Patent
James et al.

(10) Patent No.: US 12,276,628 B2
(45) Date of Patent: *Apr. 15, 2025

(54) SYSTEMS AND METHODS FOR MEASURING ELECTRICAL CHARACTERISTIC OF MEDICAL FLUIDS

(71) Applicant: Fresenius Medical Care Holdings, Inc., Waltham, MA (US)

(72) Inventors: Philip Scott James, Orinda, CA (US); Jon F. Moss, Antioch, CA (US); Lynn E. Jensen, Syracuse, UT (US); Mary Hoover, Shawnee, OK (US); Spencer Barrett, Oklahoma City, OK (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/500,755

(22) Filed: Nov. 2, 2023

(65) Prior Publication Data

US 2024/0060924 A1 Feb. 22, 2024

Related U.S. Application Data

(63) Continuation of application No. 16/854,745, filed on Apr. 21, 2020, now Pat. No. 11,879,860.

(Continued)

(51) Int. Cl.
*G01N 27/07* (2006.01)
*A61M 1/02* (2006.01)
(Continued)

(52) U.S. Cl.
CPC ............... *G01N 27/07* (2013.01); *A61M 1/02* (2013.01); *A61M 1/152* (2022.05); *A61M 1/159* (2022.05);
(Continued)

(58) Field of Classification Search
None
See application file for complete search history.

(56) References Cited

U.S. PATENT DOCUMENTS

| 3,365,659 A | 1/1968 | Wolfram |
| 3,965,414 A | 6/1976 | Teass, Jr. |

(Continued)

FOREIGN PATENT DOCUMENTS

| CN | 203923708 | 11/2014 |
| CN | 107860799 | 3/2018 |

(Continued)

OTHER PUBLICATIONS

[No Author Listed] [online], "Pogo Pins in Action," Posted on Aug. 6, 2013, retrieved on Mar. 2, 2022, <https://www.youtube.com/watch?v=XfxvxwSIjrU>, 1 page [Video Submission].

(Continued)

*Primary Examiner* — Richard C Gurtowski
(74) *Attorney, Agent, or Firm* — Fish & Richardson P.C.

(57) ABSTRACT

A device for measuring conductivity of a fluid. The device including a chamber and at least two electrodes. The chamber includes an inlet, an outlet, an upper surface, and a lower surface that runs separate from the upper surface. The fluid enters the chamber through the inlet and flows out of the chamber through the outlet. Moving along a length of the chamber from the inlet to the outlet or from the outlet to the inlet, a distance between the upper surface and the lower surface changes in at least one dimension of the chamber. The two electrodes are configured to measure electrical voltage in the fluid that enters the chamber through the inlet and flows out of the chamber through the outlet.

25 Claims, 5 Drawing Sheets

Related U.S. Application Data (60) Provisional application No. 62/860,046, filed on Jun. 11, 2019.

(51) Int. Cl.
*A61M 1/14* (2006.01)
*A61M 1/16* (2006.01)
*A61M 1/28* (2006.01)
*G01N 33/49* (2006.01)

(52) U.S. Cl.
CPC ............. *A61M 1/16* (2013.01); *A61M 1/28* (2013.01); *G01N 33/49* (2013.01); *A61M 1/1562* (2022.05); *A61M 2205/3327* (2013.01); *A61M 2205/505* (2013.01); *A61M 2205/52* (2013.01)

(56) References Cited

U.S. PATENT DOCUMENTS

| | | | |
|---|---|---|---|
| 4,808,930 | A | 2/1989 | Kaiser |
| 4,808,931 | A | 2/1989 | Ling |
| 5,008,627 | A | 4/1991 | Tsutsuta et al. |
| 5,583,432 | A | 12/1996 | Barnes |
| 5,708,363 | A | 1/1998 | Yates et al. |
| 6,690,172 | B2 | 2/2004 | Higo |
| 11,879,860 | B2 * | 1/2024 | James ............... A61M 1/16 |
| 2003/0059945 | A1 | 3/2003 | Dzekunov et al. |
| 2004/0254513 | A1 | 12/2004 | Shang et al. |
| 2006/0133176 | A1 | 6/2006 | Kim |
| 2006/0275907 | A1 | 12/2006 | Glocker |
| 2006/0275917 | A1 | 12/2006 | Glocker |
| 2007/0024287 | A1 | 2/2007 | Graves et al. |
| 2011/0154910 | A1 | 6/2011 | Murata |
| 2013/0213891 | A1 | 8/2013 | Karoor |
| 2013/0271149 | A1 | 10/2013 | Lord, III et al. |
| 2014/0112828 | A1 | 4/2014 | Grant et al. |
| 2017/0173262 | A1 | 6/2017 | Veltz |
| 2017/0182235 | A1 | 6/2017 | Weaver et al. |
| 2017/0216512 | A1 | 8/2017 | Kopperschmidt |
| 2018/0278050 | A1 | 9/2018 | Rabier |
| 2022/0218888 | A1 | 7/2022 | Barrett et al. |

FOREIGN PATENT DOCUMENTS

| | | |
|---|---|---|
| EP | 2143378 | 1/2010 |
| GB | 1517697 | 7/1978 |
| GB | 2064779 | 6/1981 |
| KR | 10-2009-0129577 | 12/2009 |
| RU | 2597067 | 9/2016 |
| WO | WO 93/18395 | 9/1993 |
| WO | WO 00/27199 | 5/2000 |

OTHER PUBLICATIONS

[No Author Listed] [online], "Swift-Dock—spring loaded interface assemblies for docking stations," Posted on Oct. 11, 2016, retrieved on Mar. 2, 2022, <https://www.youtube.com/watch?v=1K7RkjL87Dg>, 1 page [Video Submission].

International Preliminary Report on Patentability in International Appln. No. PCT/US2020/029153, mailed Dec. 23, 2021, 8 pages.

Keim, "Measuring Resistance, in Circuit and Out—Technical Articles," Jun. 21, 2015, retrieved on Oct. 25, 2019, retrieved from URL <https://www.allaboutcircuits.com/technical-articles/measuring-resistance-in-circuit-and-out/>, 4 pages.

PCT International Search Report and Written Opinion in Appln. No. PCT/US2020/029153, dated Jul. 15, 2020, 10 pages.

Sharp et al., "Tissue type determination by impedance measurement: A bipolar and monopolar comparison," Saudi J Anaesth., Jan.-Mar. 2017, 11(1):15-20.

* cited by examiner

SYSTEMS AND METHODS FOR MEASURING ELECTRICAL CHARACTERISTIC OF MEDICAL FLUIDS

CROSS-REFERENCE TO RELATED APPLICATIONS

This application is a continuation application of and claims the benefit of priority to U.S. application Ser. No. 16/854,745, filed on Apr. 21, 2020, which claims priority to U.S. Patent Application Ser. No. 62/860,046, filed on Jun. 11, 2019, the entire contents of which are hereby incorporated by reference.

TECHNICAL FIELD

This invention relates to measuring conductivity of a medical fluid.

BACKGROUND

During hemodialysis, impurities and toxins are removed from the blood of a patient by drawing the blood out of the patient through a blood access site, typically via a catheter, and then passing the blood through an artificial kidney (often referred to as a "dialyzer"). The artificial kidney includes a semi-permeable membrane that separates a first conduit from a second conduit. Generally, a dialysis solution (often referred to as a "dialysate") flows through the first conduit of the dialyzer while the patient's blood flows through the second conduit of the dialyzer, causing impurities and toxins to be transferred from the blood to the dialysate through the semi-permeable membrane. The impurities and toxins can, for example, be removed from the blood by a diffusion process. After passing through the dialyzer, the purified blood is then returned to the patient.

Maintaining a substantially constant concentration of sodium in the patient's blood throughout the hemodialysis treatment can help to reduce or prevent discomfort experienced by the patient. Therefore, sodium concentrations in the patient's blood and in the dialysate can be monitored during hemodialysis treatment.

SUMMARY

Implementations of the present disclosure are directed to a disposable device for measuring electrical characteristics of medical fluids, such as blood in dialysis systems. The device has a configuration that directs bubbles in the fluid away from electrodes that measure the electrical characteristics of the fluid.

In some implementations, the disposable device that includes a chamber and two electrodes. The chamber including an inlet, an outlet, an upper surface, and a lower surface that runs separate from the upper surface. The fluid enters the chamber through the inlet and flows out of the chamber through the outlet. Moving along a length of the chamber from the inlet to the outlet or from the outlet to the inlet, a distance between the upper surface and the lower surface changes in at least one dimension of the chamber. The two electrodes are configured to measure electrical voltage in the fluid that enters the chamber through the inlet and flows out of the chamber through the outlet. Other implementations include corresponding methods and systems configured to perform the actions needed to measure electrical characteristics of fluid.

In some embodiments, the chamber is disposable and is calibrated for a specific cell constant that is determined based on location of the two electrodes with respect to each other. In some examples, conductivity of the fluid is determined by dividing the constant cell to an impedance of the fluid, the impedance being determined based on the measured electrical voltage.

Some embodiments include an air detector sensors configured to detect that at least one of the two electrodes is exposed to air. The air detector sensor can include at least two sensor electrodes, each sensor electrode including having a respective conductive tip configured to receive or transmit an electrical current when sunk in a non-gaseous environment.

In some embodiments, the upper surface is in a concave shape. In some embodiments, the chamber has a curved side wall that connects the upper surface to the lower surface. The side wall may form an elliptical cross section for the chamber. In some embodiments, the length of the chamber is less than 5 centimeters.

Some embodiments include two additional electrodes, wherein the two electrodes measure the electrical voltage when the two additional electrodes apply the electrical current to the fluid.

The inlet can be connected to a peristaltic pump configured to pump the fluid into the chamber.

The device is attachable to a dialysis system. For example, the chamber may be formed in a cassette that is insertable into the dialysis system. The dialysis system can be a hemodialysis system or can include a peritoneal dialysis machine.

The present disclosure also describes methods of measuring conductivity of a fluid. One method includes receiving, through an inlet of a chamber, the fluid, wherein the fluid flows within the chamber and about multiple electrodes located in the chamber; applying an electrical current to first two electrodes of the multiple electrodes; measuring an electrical voltage between second two electrodes of the multiple electrodes; and measuring electrical conductivity of the fluid based on the applied electrical current and the measured electrical voltage, wherein the chamber is designed so that bubbles within the fluid are directed away from the electrodes.

This and other methods described herein can optionally include one or more of the following actions: the method includes pumping the fluid out of the chamber by applying pressure pulses to the fluid; the method includes detecting, by at least two air detector sensors, that at least a tip of at least one electrode is exposed to air; each of the air detector sensors has a height that is equal or larger than a height of the at least one electrode, the heights being measured in a direction perpendicular to a bottom surface of the chamber; the fluid comprises a medical fluid or blood; the chamber has an upper surface, and a lower surface that runs separate from the upper surface, and moving along a length of the chamber from the inlet to the outlet or from the outlet to the inlet, a distance between the upper surface and the lower surface changes in at least one dimension of the chamber.

Devices and methods in accordance with the present disclosure may include any combination of the aspects and features described herein. That is, devices in accordance with the present disclosure are not limited to the combinations of aspects and features specifically described herein, but also include any combination of the aspects and features provided.

Implementations of the present disclosure provide one or more of the following technical advantages and/or technical improvements over previously available solutions. The implementations allow monitoring fluid parameters (e.g., concentration, fluid elements, etc.) of a medical fluid by measuring electrical characteristics of the fluid. For example, a dialysate should have a conductivity that indicates that a certain amount and ratio of sodium bicarbonate is present, because an imbalance could impact the health of the patient and cause discomfort. The present implementations provide a contactless sensor that can measure conductivity of the dialysate without making direct contact (e.g., via electrodes) with the patient's body.

The implementations include a pre-calibrated and disposable data collecting cell that collects data of the fluid's electrical characteristics (e.g., electrical voltage). The pre-calibrated cell eliminates a need to calibrate the cell for each use, which makes it easier for an unsophisticated patient to use the cell at home and without assistance of a medical staff. For example, a patient may insert or attach the cell to a dialysis system to monitor their blood parameters and adjust the dialysis system accordingly without being worried about calibrating the cell before use. In addition, the cell can be very light weighted and substantially small, which makes it easy to carry, store, and use. Further, the cell is designed to improve accuracy in measuring the fluid's electrical characteristics by directing gas (e.g., air) bubbles away from the cell's electrodes.

The details of one or more implementations of the present disclosure are set forth in the accompanying drawings and the description below. Other features and advantages of the present disclosure will be apparent from the description and drawings, and from the claims.

DESCRIPTION OF DRAWINGS

Like reference symbols in the various drawings indicate like elements.

DETAILED DESCRIPTION

Implementations of the present disclosure provide a device that can be used to measure one or more electrical characteristics (e.g., electrical conductivity) of fluids such as blood in dialysis systems. The device has a disposable data collecting cell that can be replaced after a certain number of uses, for example, after every use. The cell includes a chamber with an inlet and an outlet. Fluid enters the chamber through the inlet and flows out of the chamber through the outlet. Multiple electrodes are located within the chamber to measure electrical characteristics of the fluid.

The chamber is designed to direct bubbles within the fluid away from the electrodes. In some implementations, moving along the length of the chamber from the inlet to the outlet, a distance between an upper surface and a lower surface of the chamber varies so that the bubbles would be directed from the lower distance region to the higher distance region. The electrodes can be located at the lower distance region of the chamber. For example, the upper surface of the chamber can be in concave shape and the electrodes can be located away from edges of the concaved upper surface to which the bubbles are directed.

Figure 1:
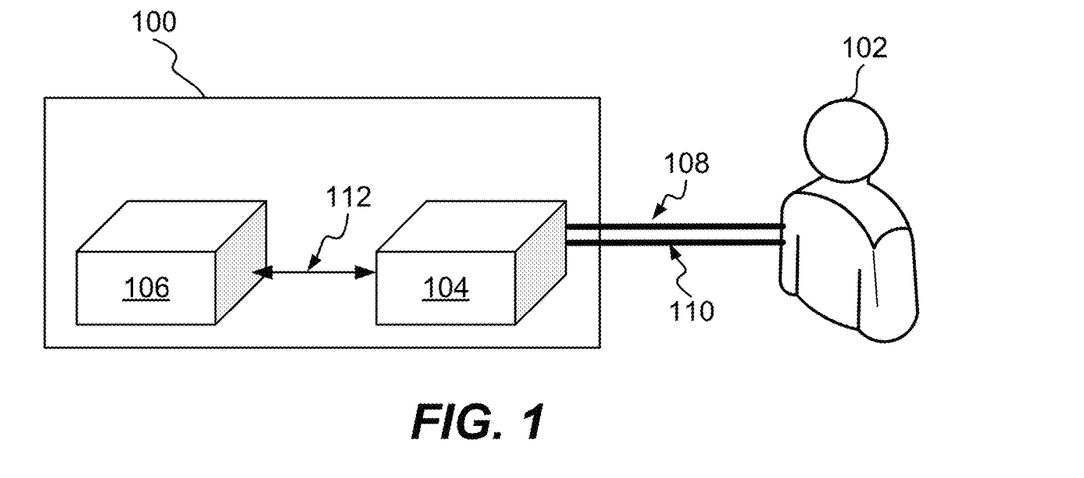
FIG. 1 depicts an example application of the implementations of the present disclosure.

FIG. 1 depicts an example application of the implementations of the present disclosure. As depicted, a system 100 is connected to a patient 102. The system 100 can include a dialysis system (e.g., a peritoneal dialysis machine) to dialyze the patient's blood. The system 100 includes a data collecting unit 104, and a measurement unit 106.

Patient's blood flows from the patient 102's body to the data collecting unit 104 through a first conduit 108, and flows back from the data collecting unit 104 to the patient's body through a second conduit 110. During this process, the data collecting unit 104 collects data of the patient's blood. Data collected by the data collecting unit 104 is transferred to the measurement unit 106 through the communication channel 112. The communication channel can be a wired and/or a wireless channel.

The measurement unit 106 includes one or more devices to measure electrical characteristic(s) of the blood based on the data received from the data collecting unit 104. For example, the measurement unit 106 can include an impedance analyzer to measure impedance or conductivity of the blood. The measurement unit 106 can also include one or more power supplies that generate an electrical current, which is transmitted through the communication channel 112 to the data collecting unit 104 to excite the blood.

Figure 2:
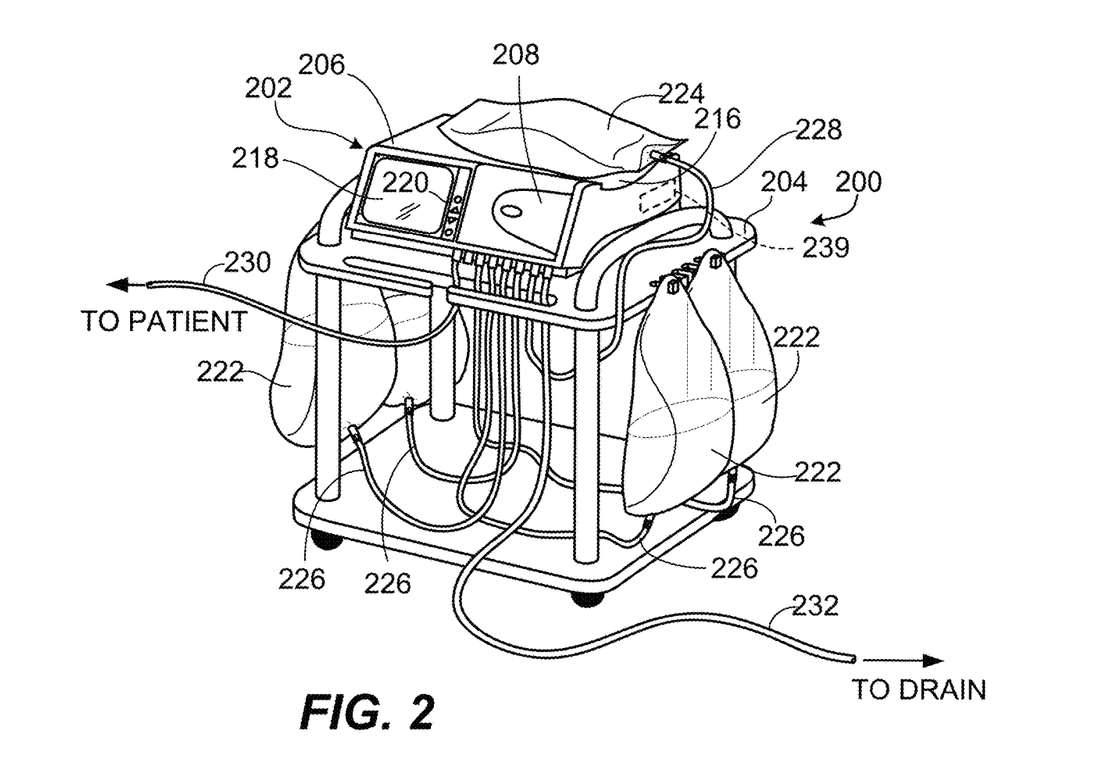
FIG. 2 illustrates an example of a peritoneal dialysis (PD) system.

FIG. 2 shows an example of the system 100 of FIG. 1. In particular, FIG. 2 shows an example peritoneal dialysis system 200 that can may include the data collecting unit 104 and the measurement unit 106 described above. The peritoneal dialysis system 200 includes a PD machine (also generally referred to as a PD cycler) 202 seated on a cart 204. The PD machine 202 includes a housing 206, a door 208, and a cassette interface 210 that contacts a disposable PD cassette 212 when the cassette 212 is disposed within a cassette compartment 214 formed between the cassette interface 210 and the closed door 208. A heater tray 216 is positioned on top of the housing 206. The heater tray 216 is sized and shaped to accommodate a bag of PD solution such as dialysate (e.g., a 5 liter bag of dialysate). The PD machine 202 also includes a user interface such as a touch screen display 218 and additional control buttons 220 that can be operated by a user (e.g., a caregiver or a patient) to allow, for example, set up, initiation, and/or termination of a PD treatment.

Dialysate bags 222 are suspended from fingers on the sides of the cart 204, and a heater bag 224 is positioned in the heater tray 216. The dialysate bags 222 and the heater bag 224 are connected to the cassette 212 via dialysate bag lines 226 and a heater bag line 228, respectively. The dialysate bag lines 226 can be used to pass dialysate from dialysate bags 222 to the cassette 212 during use, and the heater bag line 228 can be used to pass dialysate back and forth between the cassette 212 and the heater bag 224 during use. In addition, a patient line 230 and a drain line 232 are connected to the cassette 212. The patient line 230 can be connected to a patient's abdomen via a catheter and can be used to pass dialysate back and forth between the cassette 212 and the patient's peritoneal cavity during use. The catheter may be connected to the patient line 230 via a port such as a fitting. The drain line 232 can be connected to a drain or drain receptacle and can be used to pass dialysate from the cassette 212 to the drain or drain receptacle during use.

The PD machine 202 also includes a control unit 239 (e.g., a processor). The control unit 239 can receive signals from and transmit signals to the touch screen display 218, the control panel 220, and the various other components of the PD system 200. The control unit 239 can control the operating parameters of the PD machine 102. In some implementations, the control unit 239 is an MPC823 PowerPC device manufactured by Motorola, Inc.

Figure 3A:
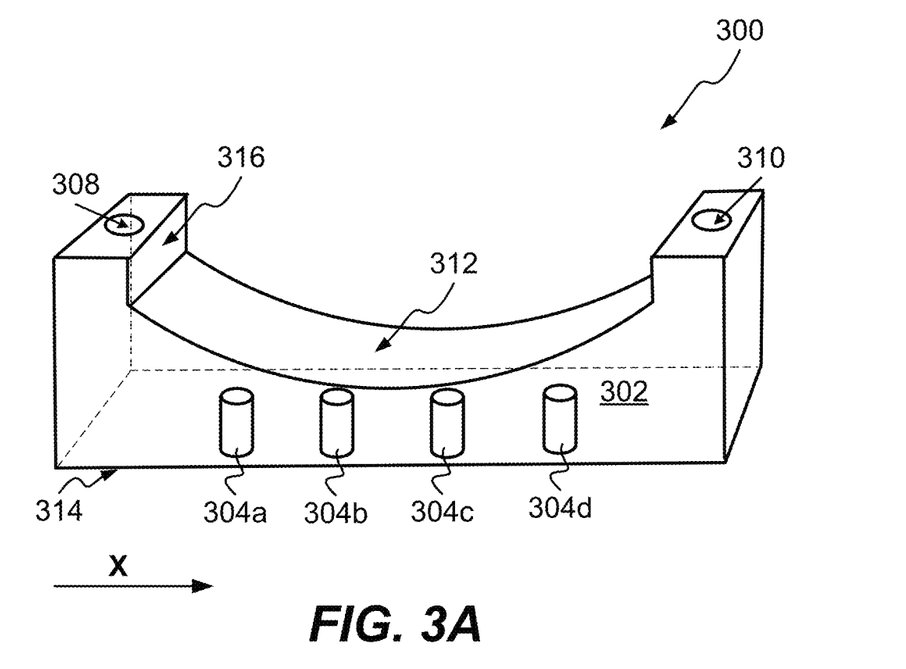
FIG. 3A illustrates a perspective views an example data collecting cell according to implementations of the present disclosure.

Referring back to FIG. 1, the data collecting unit 104 includes a data collecting cell that has multiple electrodes to electrically excite the blood and to measure electrical voltage within the blood. FIG. 3A illustrates a perspective view of an example data collecting cell 300. The cell 300 includes a chamber 302 with an inlet 308 and an outlet 310. Fluid (e.g., blood, medical fluids) enters the chamber 302 through the inlet 308 and flows out of the chamber through the outlet 310. Multiple electrodes 304a, 304b, 304c, and 304d are located within the chamber to measure electrical parameters (such as electrical voltage) of the fluid in response to applying an electrical current to the fluid.

The chamber 302 contains multiple electrodes 304a, 304b, 304c, and 304d. Two or more electrodes are used to apply electrical current to the fluid, and two or more electrodes are used to measure electrical voltage. For example, electrodes 304a and 304d can be connected to a power supply of the measurement unit 106, and electrodes 304b and 304c can be connected to a measuring device, such as an impedance analyzer, in the measurement unit 106. Alternatively, the same electrodes that apply current can also measure voltage.

The chamber 302 has an upper surface 312 and a lower surface 314. Moving along the length of the chamber from the inlet 308 to the outlet 310 (in direction x), the distance between the upper surface 312 and the lower surface 314 varies. In the illustrated example, the distance between the upper and the lower surfaces is greater at about the inlet and the outlet regions of the chamber than at the region where the electrodes are located. Such configuration directs the gas bubbles (e.g., air bubbles) in the fluid away from the electrodes and towards the outlet (or towards the inlet depending on the fluid flow's speed).

In the example cell 300, the upper surface of the chamber has a concave shape, and the distance between the upper and the lower surfaces is minimum at a region halfway between the inlet and the outlet. However, the minimum distance can be at any part of the cell. For example, the minimum distance may be in the first half of the chamber along direction x (i.e., closer to the inlet than to the outlet) or in the second half of the chamber along direction x (i.e., closer to the outlet than to the inlet).

In the example cell 300, the distance between the upper and the lower surfaces is greatest close to the inlet and the outlet regions of the chamber. In other embodiments, the greatest distance may be at any part of the chamber, e.g., other than where the electrodes are located. In other words, the upper surface 212 is not at its greatest distance from the lower surface 214 directly above the electrodes (but does not have to be at its minimum distance directly above the electrodes, either).

The illustrated upper surface 312 of the example cell 300 is curved. Alternatively, the upper surface can be designed as a set of multiple inclined plates. For example, the upper surface can include two diverging plates that intersect at a common line at a region between the inlet and outlet (along direction x), forming a V-shape upper surface. An upper surface of a cell can have a combination of curved and plate surfaces.

The illustrated upper surface 212 in FIG. 3A is connected to the inlet and the outlet by respective connector walls 316. Alternatively, one or both of the connector walls can be eliminated so that the inlet and/or the outlet is formed on a portion of the upper surface 312.

Figure 3B:
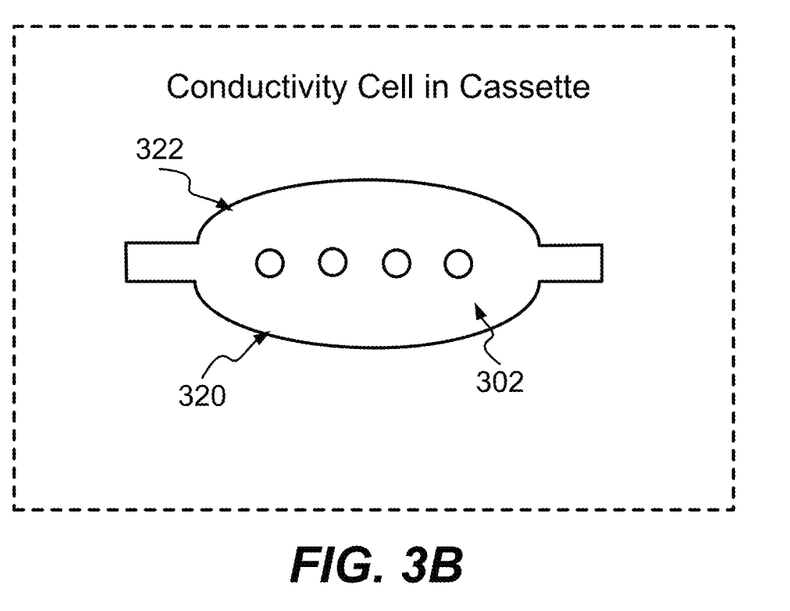
FIG. 3B illustrates a bottom view of the data collecting cell of FIG. 3A.

The upper surface 312 is connected to the bottom surface 314 through side walls of the chamber (now shown in FIG. 23A). FIG. 3B illustrates a bottom view of the cell 300 that depicts a bottom profile of the side walls 320 and 322. As illustrated, the side walls 320 and 322 of the chamber are curved. For example, the chamber 302 can have an elliptical cross section. Curved side walls help in reducing turbulent fluid flow and provide a laminar fluid flow through the chamber.

Figure 4:
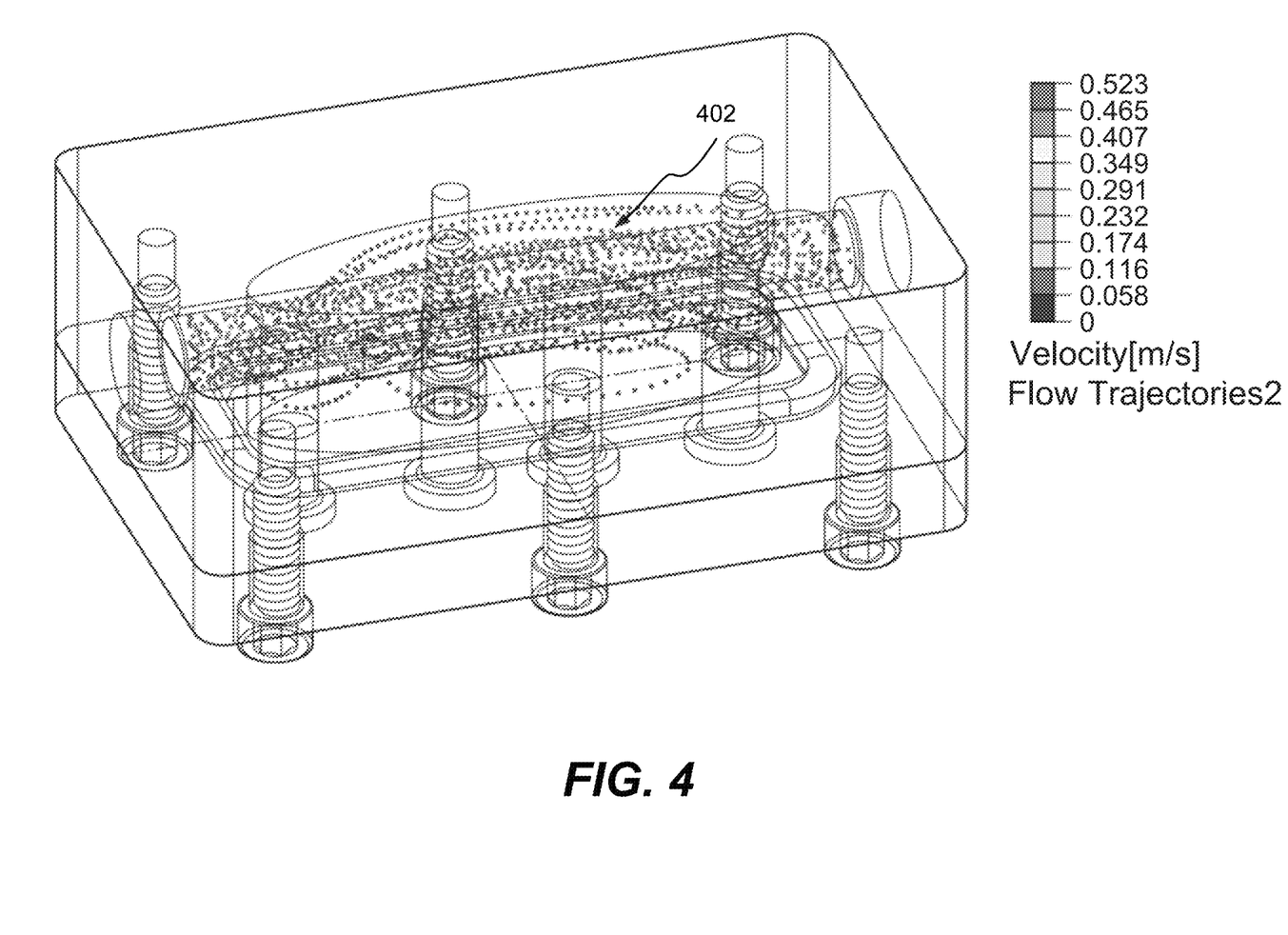
FIG. 4 illustrates fluid flow in an example data collecting cell according to implementations of the present disclosure.

FIG. 4 illustrates fluid flow in an elliptical chamber 402. As illustrated, since the chamber 402 does not have any corners, the fluid does not get trapped in any particular part of the chamber, and rather flows smoothly throughout the chamber.

Referring back to FIG. 3A, the example cell 300 includes four electrodes, however, cells with more or less number of electrodes (e.g., two or three electrodes) can also be designed. For example, a cell can be designed to have only two electrodes, where the same electrodes apply the electrical current and measure the voltage of the two electrodes. Additional electrodes (e.g., four) can improve measurement accuracy as separate set of electrodes can be used for applying current and measuring voltage. Relatively fewer electrodes (e.g., two) can help in reducing the size of the cell.

Once connected to the power supply, the cell 302 can provide an excitation electrical current to the fluid. The electrical current can have a frequency ranging from DC to 100 kHz. The excitation current can be in any bipolar or unipolar AC form such as sinusoidal, sawtooth, square wave shape, etc.

The excitation current that is being applied to the electrodes can be limited to a predetermined threshold. The threshold can be below 50 milliAmpere (mA), e.g., 10 mA. Limiting the current to a low threshold value guaranty safety in handling the device. Further, a chance of electrical shortening or damages by the exposed electrode contacts can be reduced by limiting the current that can pass through the circuitry that transmits current from the power supply to the cell. For example, the circuitry can have bidirectional diodes that limit the maximum voltage across different sections of the circuit to a threshold voltage, e.g., 1 volt.

As noted above, the data collecting cell is disposable and can be detached from system 100 (e.g., a dialysis system, such as the PD system 200 of FIG. 2) after a certain number of uses (e.g., one-time use). The each cell can be pre-calibrated during the manufacturing process before being provided to consumers. This feature provides a consumer-friendly feature that allows patients to replace the cell after a certain number of use without being worried about recalibrating the cell before each use.

To eliminate a need to calibrate the data collection cell for each use, each cell can be designed for a specific cell constant. The calibration can stay accurate for a predetermined number of use, and the cell can be disposed afterwards. For example, a cell may be calibrated for 13.8 millisiemens (mS) and may be set for one time use. The calibration may be set for a specific temperature, e.g., 37 Celsius, and/or a specific type of fluid (e.g., blood, urine, saline, etc.).

A cell constant (that is used to calibrate a cell) is a measurement of the fluid volume contained between the two measuring electrodes, for example, electrodes 304b and 304c that measure the electrical voltage. A data collecting cell may be designed for a particular cell constant. Parameters of the measurement unit 106 to which the data collecting cell is to be attached, may determine the particular cell constant. For example, the data collecting cell can be designed to have a cell constant between 12-16 millisiemens (mS), for example, 14 mS.

A cell constant of a data collecting cell depends on the geometry of and the distance between two measuring electrodes of the cell. The electrodes can have any shape. However, electrodes with curved cross section (e.g., cylindrical electrodes similar to the electrodes depicted in FIGS. 3A and 3B) are preferred to electrodes that have one or more corners (e.g., cubic or pyramid shaped electrodes) because curvature reduces fluid turbulence in the chamber as compared to edges.

Electrical conductivity of a fluid in a cell can be calculated based on the cell constant of the cell using the following formula:

$$\text{Conductivity} = \frac{K}{\text{Resistance}} = \frac{K}{Z * \cos(\Phi)}. \quad \text{Equation 1}$$

where K is the cell constant, Z is an impedance (e.g., in ohm) of the fluid, and $\Phi$ is phase angle (e.g., in degrees). Conductivity can be measured in milliSiemens per centimeter (mS/cm).

In order to get an accurate measurement of the fluid's electrical characteristics, at least the measuring electrodes that measure electrical voltage (or at least the conductive portion of the measuring electrodes) should be completely immersed/sunk in the fluid. An exposure of a conductive portion of a measuring electrode to air can lead to inaccuracy in measuring electrical characteristics of the fluid.

Figure 5:
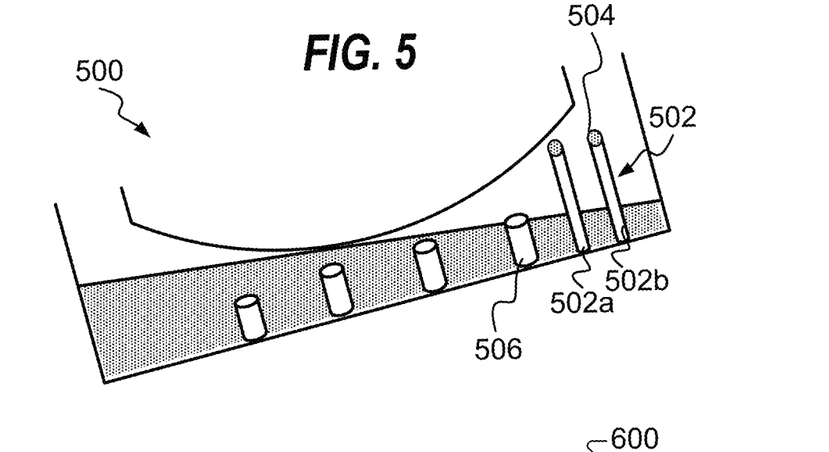
FIG. 5 illustrates an example data collecting cell including a gas detector sensor according to implementations of the present disclosure.

A data collecting cell can include a gas detector sensor that alerts an exposure of one or more electrodes to air (or to other gasses within the chamber, or to vacuum). FIG. 5 illustrates an example data collecting cell 500 including a gas detector sensor 502 within the cell's chamber. The gas detector sensor 502 includes multiple sensor electrodes 502a and 502b. Each sensor electrode is an insulated conductors and has a respective conductive portion. The conductive portions are configured to transmit an electrical current when sunk in a fluid. However, no current is transmitted between the conductive portions of the two sensor electrodes when the conductive portions are exposed to a gaseous environment such as air. Accordingly, when no current is transmitted between the sensor electrodes, the sensor 502 detects that the fluid level is too low and at least one of the measuring electrodes is exposed to air.

In the example data collecting cell 500, the conductive portions of the sensor electrodes 502a and 502b are at their respective tips 504. At least one of the two sensor electrodes 502a and 502b can be designed to be taller than at least one of the measuring electrodes (e.g., the measuring electrode 506) of the cell 500 in order to detect situations when the measuring electrode (or a portion of it) is exposed to air. For example, in the tilted position illustrated in FIG. 5, the fluid level is dropped below the measuring electrode 506's height, causing a portion of the measuring sensor 506 to stick out of the fluid and be exposed to air.

In some embodiments, the sensor electrodes are taller than any of the excitation electrodes (i.e., electrodes that apply the excitation electrical current) or measuring electrodes (i.e., electrodes that measure electrical voltage,) of the cell. In some embodiments, two or more sensor electrodes are assigned to particular excitation or measuring electrode(s). For example, the electrodes 502a and 502b may be set to detect exposure of electrode 406 to air, irrespective of whether or not any other electrode is sunk in the fluid or exposed to air.

Referring back to FIGS. 1 and 3A, the system 100 can also include a pump configured to pressurize the fluid inside the data collecting cell 300 of the data collecting unit 104. The pump (not shown) can be attached to the data collecting unit 104, or either of the first or the second conduits 108, 110. The pump can be a peristaltic pump that applies pressure pulses to the fluid. Such pulses force gas bubbles that are attached to any part of the data collecting cell (e.g., the electrodes, the side walls, or the lower or upper surfaces of the chamber,) to be detached and be moved towards the outlet. Using peristaltic pumps is particularly helpful in removing smaller bubbles that may be harder to remove, especially in a constant or low-speed fluid current.

The cell's size and weight are substantially small, which provide convenient handling and carrying by a single person. For example, the device can have dimensions smaller than 5 cm×5 cm×5 cm (e.g., 1 cm×3 cm×3 cm), and can be made of plastic.

Figure 6:
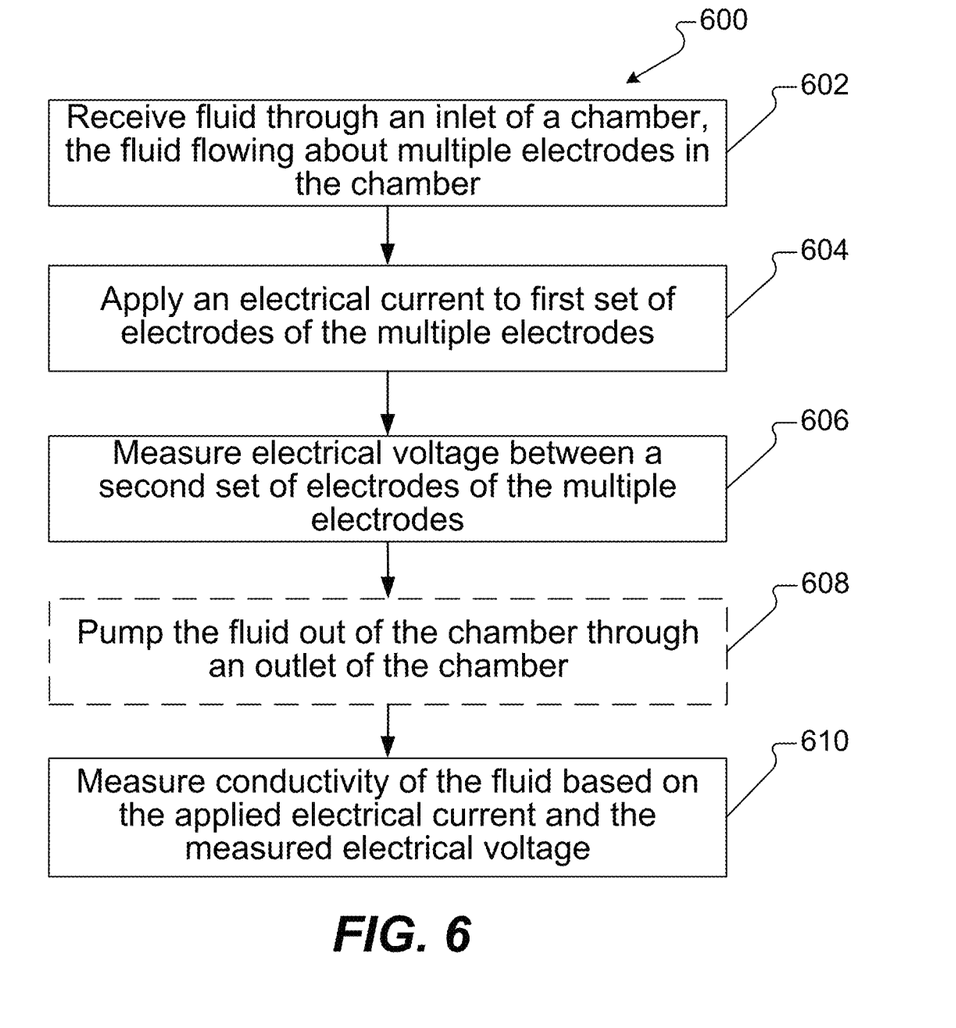
FIG. 6 depicts an example process that can be executed in accordance with the implementations of the present disclosure.

FIG. 6 depicts an example process 600 that can be executed in accordance with the implementations of the present disclosure. The process 600 can be implemented by system 100 (e.g., the PD system 200) including the data collecting cell 300, or by any other system capable of performing the process 600.

In this process, fluid is received through an inlet of a chamber and flows about multiple electrodes located within the chamber (602). For example, fluid can be received at the chamber 302 through the inlet 308. The fluid passes through the chamber and about the electrodes 304a through 304d. The electrodes can be connected to a measurement unit, a power supply, and/or a dialysis machine.

An electrical current is applied to a first set of electrodes within the chamber (604). For example, the electrodes 304a and 304d may transmit electrical current through the fluid within the chamber. The electrodes 304a and 304d are connected to a power supply, for example, located in the measurement unit 106.

Electrical voltage is measured between a second set of electrodes within the chamber (606). For example, the electrodes 304b and 304c can measure the electrical voltage upon the application of an electrical current to the fluid. The second set of electrodes can be the same or different from the first set of electrodes. Having the two sets separate would improve measurement accuracy but would also increase the chamber size needed for setting the electrodes.

Fluid can be pumped out of the chamber through an outlet of the chamber (608). For example, pressure pulses can be applied to the fluid to pump the fluid out of the chamber. Such pressure pulses help in removing small bubbles from the fluid.

Conductivity (or any other desired electrical characteristics) of the fluid is measured (or calculated) based on the applied electrical current and the measured electrical voltage (610). For example, the electrodes that measured the electrical voltage can transmit their measured data to a measurement unit (e.g., an impedance analyzer) to calculate the conductivity of the current.

The chamber is designed so that bubbles within the fluid are directed away from the electrodes. For example, the chamber can have a lower surface, and an upper surface separated from the lower surface. In some implementations, the lower surface is parallel to a portion of the upper surfaces in which the inlet and outlet are formed. Moving along a length of the chamber from the inlet to the outlet, a distance between the upper surface and the lower surface changes in at least one dimension of the chamber (e.g., in a direction perpendicular to the lower surface). The upper surface can be similar to the upper surface 312 in FIG. 3A.

Figure 7:
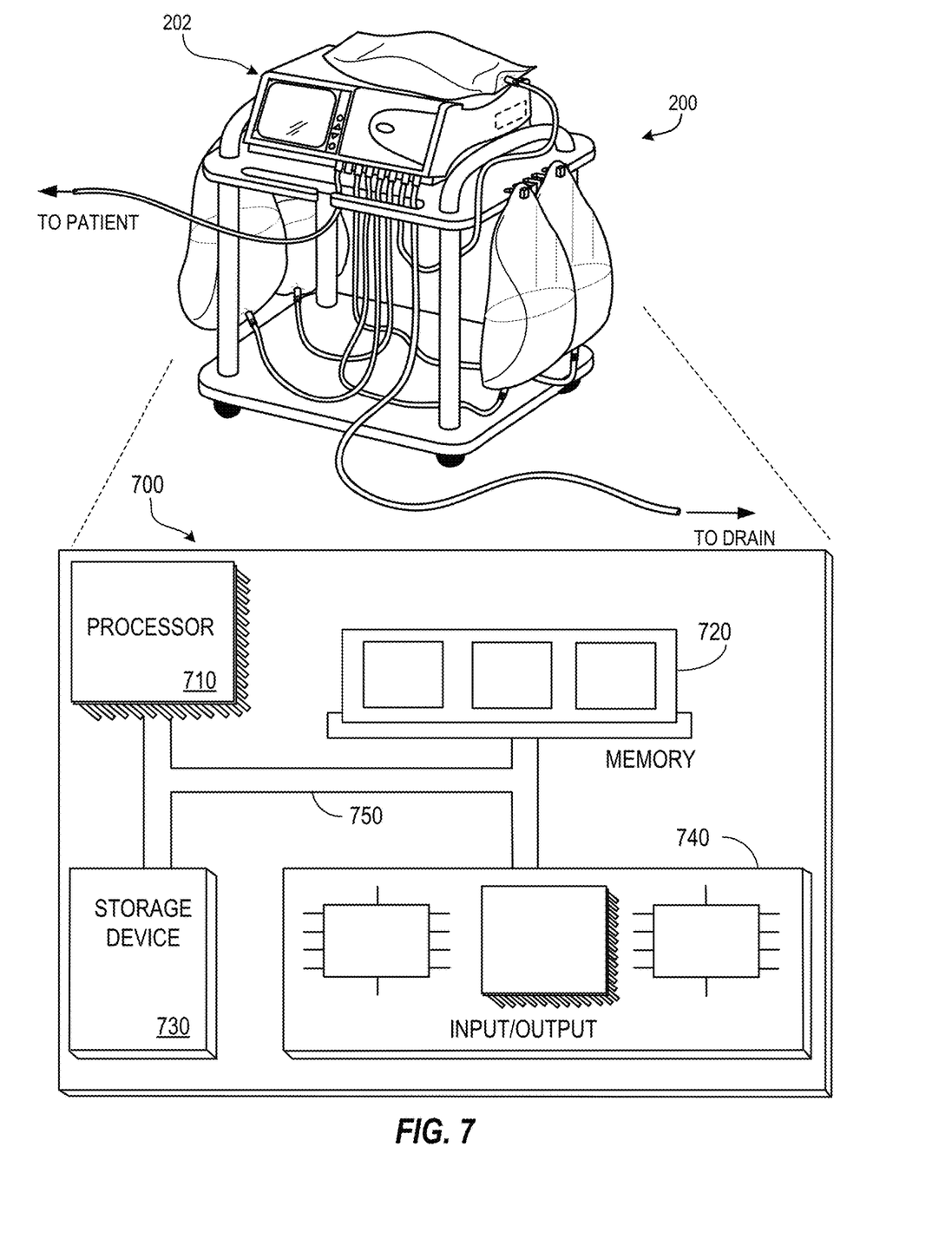
FIG. 7 shows an example of a computer system and related components.

FIG. 7 is a block diagram of an example computer system 700 that can be used as part of the system 100 of FIG. 1, for example to perform the measurements or analysis of the measurement unit 106. For example, a control unit, a computing device, and/or a microcontroller could be examples of the system 700 described here. The system 700 includes a processor 710, a memory 720, a storage device 730, and an input/output device 740. Each of the components 710, 720, 730, and 740 can be interconnected, for example, using a system bus 750. The processor 710 is capable of processing instructions for execution within the system 700. The processor 710 can be a single-threaded processor, a multi-threaded processor, or a quantum computer. The processor 710 is capable of processing instructions stored in the memory 720 or on the storage device 730. The processor 710 may execute operations such as causing the dialysis system to carry out dialysis functions.

The memory 720 stores information within the system 700. In some implementations, the memory 720 is a computer-readable medium. The memory 720 can, for example, be a volatile memory unit or a non-volatile memory unit. In some implementations, the memory 720 stores information for causing the pumps of the dialysis system to operate as described herein.

The storage device 730 is capable of providing mass storage for the system 700. In some implementations, the storage device 730 is a non-transitory computer-readable medium. The storage device 730 can include, for example, a hard disk device, an optical disk device, a solid-date drive, a flash drive, magnetic tape, or some other large capacity storage device. The storage device 730 may alternatively be a cloud storage device, e.g., a logical storage device including multiple physical storage devices distributed on a network and accessed using a network.

The input/output device 740 provides input/output operations for the system 700. In some implementations, the input/output device 740 includes one or more of network interface devices (e.g., an Ethernet card), a serial communication device (e.g., an RS-232 10 port), and/or a wireless interface device (e.g., an 802.11 card, a 3G wireless modem, or a 4G wireless modem). In some implementations, the input/output device 740 may include short-range wireless transmission and receiving components, such as Wi-Fi, Bluetooth, and/or near field communication (NFC) components, among others. In some implementations, the input/output device includes driver devices configured to receive input data and send output data to other input/output devices, e.g., keyboard, printer and display devices (such as the touch screen display 118). In some implementations, mobile computing devices, mobile communication devices, and other devices are used.

In some implementations, the system 700 is a microcontroller. A microcontroller is a device that contains multiple elements of a computer system in a single electronics package. For example, the single electronics package could contain the processor 710, the memory 720, the storage device 730, and input/output devices 740.

The measurement unit and/or the data collection unit described herein can be part of any medical system, such as dialysis systems (e.g., a hemodialysis system), a heart lung machine, a chemotherapy system, or any other system that introduces fluid into body.

While blood was used herein as an example fluid for describing the functionality of the embodiments, the data collecting unit, in general, and the data collecting cell, in particular, can be used for determining electrical characteristics of any other type of fluids, or any medical fluids such as plasma, saline, or urine, to name a few.

A number of embodiments of the invention have been described. Nevertheless, it will be understood that various modifications may be made without departing from the spirit and scope of the invention. Accordingly, other embodiments are within the scope of the following claims.

What is claimed is:

1. A device for measuring conductivity of a fluid, the device comprising:
 a chamber that includes:
  an inlet;
  an outlet, wherein the fluid enters the chamber through the inlet and flows out of the chamber through the outlet; and
  a concave surface located between the inlet and the outlet such that bubbles in the fluid are directed along the concave surface and towards the outlet or the inlet, wherein the concave surface extends toward a base of the chamber; and
 two electrodes configured to measure electrical voltage in the fluid that enters the chamber through the inlet and flows out of the chamber through the outlet.

2. The device of claim 1, wherein the chamber is disposable and is calibrated for a specific cell constant that is determined based on a location of the two electrodes with respect to each other.

3. The device of claim 1, further comprising an air detector sensor configured to detect that at least one of the two electrodes is exposed to air.

4. The device of claim 3, wherein the air detector sensor comprises at least two sensor electrodes, each sensor electrode including a respective conductive portion configured to receive or transmit an electrical current when sunk in a non-gaseous environment.

5. The device of claim 1, wherein the chamber has a curved side wall that connects the concave surface to the base of the chamber that runs separate from the concave surface.

6. The device of claim 5, wherein the side wall forms an elliptical cross section for the chamber.

7. The device of claim 1, further comprising two additional electrodes, wherein the two electrodes measure the electrical voltage when the two additional electrodes apply an electrical current to the fluid.

8. The device of claim 1, wherein the inlet is connected to a peristaltic pump configured to pump the fluid into the chamber.

9. The device of claim 1, wherein the length of the chamber is less than 5 centimeters.

10. The device of claim 1, wherein the device is configured to be attached to a dialysis system.

11. The device of claim 10, wherein the chamber is formed in a cassette that is insertable into the dialysis system.

12. The device of claim 10, wherein the dialysis system includes a peritoneal dialysis machine.

13. A method of measuring conductivity of a fluid, the method comprising:
receiving, through an inlet of a chamber, the fluid, wherein the fluid flows within the chamber and about multiple electrodes located in the chamber;
applying an electrical current to two excitation electrodes in the multiple electrodes;
measuring an electrical voltage between two measuring electrodes in the multiple electrodes; and
measuring electrical conductivity of the fluid based on the applied electrical current and the measured electrical voltage,
wherein the chamber has a surface with at least a concave portion so that bubbles within the fluid are directed away from the electrodes along the concave portion and towards the inlet or an outlet of the chamber.

14. The method of claim 13, wherein at least one of the two excitation electrodes is the same as a respective one of the two measuring electrode.

15. The method of claim 13, further comprising pumping the fluid out of the chamber by applying pressure pulses to the fluid.

16. The method of claim 13, further comprising detecting, by at least two air detector sensors, that at least a portion of at least one electrode is exposed to air.

17. The method of claim 16, wherein each of the air detector sensors has a height that is equal to or larger than a height of the at least one electrode, the heights being measured in a direction perpendicular to a bottom surface of the chamber.

18. The method of claim 15, wherein the fluid comprises a medical fluid or blood.

19. A device for measuring conductivity of a fluid, the device comprising:
a chamber that includes:
an inlet,
an outlet, wherein the fluid enters the chamber through the inlet and flows out of the chamber through the outlet,
an upper surface, wherein the upper surface includes multiple inclined plates so that bubbles in the fluid are directed towards the outlet or the inlet; and
two electrodes configured to measure electrical voltage in the fluid that enters the chamber through the inlet and flows out of the chamber through the outlet.

20. The device of claim 19, wherein at least two of the multiple inclined plates intersect at a common line at a region between the inlet and the outlet to form a V-shape portion of the upper surface.

21. The device of claim 19, wherein the upper surface also includes a curved portion.

22. The device of claim 19, further comprising an air detector sensor configured to detect that at least one of the two electrodes is exposed to air.

23. The device of claim 22, wherein the air detector sensor comprises at least two sensor electrodes, each sensor electrode including a respective conductive portion configured to receive or transmit an electrical current when sunk in a non-gaseous environment.

24. The device of claim 19, wherein the chamber has a curved side wall that connects the upper surface to a lower surface of the chamber, wherein the lower surface runs separately from the upper surface.

25. The device of claim 19, wherein the device is configured to be attached to a dialysis system.

* * * * *